United States Patent [19]

Fujiwara et al.

[11] Patent Number: 5,782,871
[45] Date of Patent: Jul. 21, 1998

[54] SAMPLING DEVICE OF SUCTION EFFUSION FLUID

[75] Inventors: Hidetaka Fujiwara; Toru Matsumoto, both of Tokyo, Japan

[73] Assignee: NEC Corporation, Tokyo, Japan

[21] Appl. No.: 804,687

[22] Filed: Feb. 25, 1997

[30] Foreign Application Priority Data

Feb. 28, 1996 [JP] Japan ................... 8-041785

[51] Int. Cl.⁶ .................................. A61M 1/00
[52] U.S. Cl. .................................. 604/313; 604/289
[58] Field of Search ................... 604/289, 311, 604/312, 313, 315, 35, 131; 600/575, 573, 577, 578, 579

[56] References Cited

U.S. PATENT DOCUMENTS

| 4,151,832 | 5/1979 | Hamer ................... 128/765 |
| 5,291,887 | 3/1994 | Stanley et al. ........... 128/637 |
| 5,417,206 | 5/1995 | Kaneyoshi ............... 604/313 |

FOREIGN PATENT DOCUMENTS

| 2-1107 | 1/1990 | Japan . |
| 2-2648 | 1/1990 | Japan . |
| 2-20510 | 2/1990 | Japan . |
| 4-253850 | 9/1992 | Japan . |

OTHER PUBLICATIONS

M. Kikuchi et al., "Novel method for non-invasive measurement of biomedical substances in blood", Jul. 23–27, 1996, pp. 57–28, 1st Pan. Pacific Symposium, Vancouver, Canada.

J. Kimura et al., "A novel blood glucose monitoring method: an isfet biosnesor application to transcutaneous effusion fluid", 1987, pp. 327–333, Symposium on Chemical Sensors, Proceedings vol. 87–9.

N. Ito et al., "Development of a transcutaneous blood–constituent monitoring method using a suction effusion fluid collction technique and an ion–sensitive field–effect transistor glucose sensor", May 1994, pp. 242–246, Medical & Biologica Engineering & Computing.

*Primary Examiner*—John G. Weiss
*Assistant Examiner*—David J. Cho
*Attorney, Agent, or Firm*—Young & Thompson

[57] ABSTRACT

A sampling device of the suction effusion fluid that is good in sampling operation efficiency. This device includes a cell with a vacuum suction port and a skin suction port, a slide valve formed in the cell, and fluid reservoirs formed in the valve. The slide valve is movable in a plane approximately parallel to the skin surface. The slide valve opens or closes a communication path communicating the skin suction port with the vacuum suction port. Each of the fluid reservoirs is alternately communicated with the skin suction port and the vacuum suction port through the communication path by sliding movement of the slide valve. Each of the fluid reservoirs stores an effusion fluid acquired from the skin surface by vacuum suction through the skin suction port. When the slide valve is located at a position where one of the fluid reservoirs is communicated with the skin suction port and the vacuum suction port, at least one of the remaining fluid reservoirs is exposed to the outside of the cell. The slide valve preferably has a rod or disk shape.

13 Claims, 7 Drawing Sheets

SAMPLING DEVICE OF SUCTION EFFUSION FLUID

BACKGROUND OF THE INVENTION

1. Field of the Invention

The present invention relates to a biochemical measuring device for clinical applications and more particularly, to a sampling device of Suction Effusion Fluid (SEF) for collecting an extremely small amount of a biomedical substance or substances.

2. Description of the Prior Art

Conventionally, as a biomedical substance of this sort, the blood sampled from a human body has been adopted. Constituent analysis of the sampled blood has been made by using a clinical or biochemical analyzer.

However, there is the need for making some operations to separate the required constituents from the sampled blood, and the blood sampling may cause invasion and infection to the human body.

Thus, based on the recent advance of the electronics technology, measuring techniques that use the SEF sampled from the skin surface of a human body instead of blood have been developed. Examples of the measuring techniques were reported in the Proceedings of the first Pan. Pacific Symposium, Vancouver, Canada, Jul. 23–27, 1986, pp. 57–58 and the Proceedings of the Symposium on Chemical Sensors, PV87-9, 1987, pp. 327–333.

The SEF is an extremely small amount of liquid that is obtained by vacuum suction through a part of the skin surface of an arm or other where the corneous layer is removed therefrom. It has been considered that the SEF is an. interstitial fluid in the hypodermic tissue or a fluid filtered under vacuum through the walls of the capillary blood vessel.

Because the SEF has a protein concentration lower than that of the blood, the amount of protein deposited onto the surface of a sensor in measurement can be reduced, providing an advantage that the service life of the sensor can be prolonged. In addition, because the SEP is sampled transcutaneously, the measuring method using the SEF, unlike the conventional one involving blood collection, has been considered advantageous from the standpoints of reducing the pain given to the subject and preventing the infection with disease germs.

FIG. 1 shows an example of the conventional SEF sampling devices. In FIG. 1, a conventional SEF sampling device 120 is equipped with a cell 121 made of a clear resin material. As the clear resin material, polyvinyl chloride, acrylic resin, or other is used. The cell 121 is composed of a cylindrical lower part (i.e., a base) 121a and a cylindrical upper part (i.e., head) 121b. The diameter of the head 121b is smaller than that of the base 121a. The head 121b is concentric with the base 121a. In other words, the base 121a and the head 121b are concentric with the vertical, central axis of the cell 121.

A circular recess 128 serving as a sampling port is formed on the bottom surface of the base 121a. A communication path 123a is formed in the base 121a to be concentric with the central axis of the cell 121. A skin suction port 123 is formed on the bottom surface of the base 121a in the sampling port 128. The port 123 is formed by the bottom opening of the communication path 123a.

A spacer 129 with fine meshes is attached to the base 121a in the recess or sampling port 128. The spacer 129 prevents the skinsurface 130 from being tightly contacted with the skin suction port 123. The tight contact of the skin surface 130 makes it difficult to sample the effusion fluid 131 in vacuum suction.

The head 121b is provided with a circular hole 121c penetrating the head 121b in a direction perpendicular to the central axis of the cell 121 (i.e., parallel to the skin surface 130).

A cylindrical slide valve 124 is inserted and fitted into the hole 121c to slide along the axis of the hole 121c. The valve 124 has a communication path 141 extending along the central axis of the cell 121.

The communication path 141 of the valve 124 is able to be connected to or disconnected from the communication path 123 (i.e., the skin suction port 123) of the base 121 a by linear sliding movement of the valve 124. Specifically, when the valve 124 is located at a position where the two paths 123a and 124 are overlapped with each other, the two paths 123a and 124 are connected to each other. When the valve 124 is not located at this point, the communication path 141 is disconnected from the communication path 123.

The valve 124 has two circular channels at each side of the communication path 141. Two O-rings 126 and 127 are fitted into the channels, respectively. Thus, the valve 124 is incorporated airtightly in the cell 121 by means of the O-rings 126 and 127.

Two handles 143 are attached to the both ends of the valve 124, respectively. The ends of the handles 143 are protruded from the hole 121c on the opposite sides. The valve 124 may be slid in the hole 121c by pressing any one of the handles 143 along the central axis of the hole 121c. The valve 124 is movable between the points where the outer ends of the two handles 143 are contacted with the head 121b.

A cylindrical fluid reservoir 125 for storing an effusion fluid 131 therein is formed in the upper part of the head 121b. The reservoir 125 is located over the slide valve 124. The top of the reservoir 125 is opened on the top end of the head 121b. The reservoir 125 is communicated with the penetrating hole 121c through a communication path 125a. The reservoir 125 and the path 125a are located on the central axis of the cell 121. The communication path 125a and the fluid reservoir 125 are able to be connected to or disconnected from the communication path 141 of the valve 124 by sliding movement of the valve 124 along the skin surface 130, specifically, when the valve 124 is located at the position where the paths 141 and 123a are overlapped with each other, the path 125a and the reservoir 125 are connected to the path 141. When the valve 124 is not located at this point, the path 125a and the reservoir 125 are disconnected from the path 141.

A circular channel is formed on the top end of the head 121b to surround the reservoir 125. An O-rings 143 is fitted into the channel.

A circular cover 142 having a circular recess in the bottom is attached onto the top of the head 121b. The recess of the cover 142 is fitted into the head 121b. The cover 142 maybe incorporated airtightly through the O-ring 143.

The cover 142 has a communication path 122a formed to be concentric with the central axis of the cell 121. The path 122a is communicated with the underlying fluid reservoir 125. A vacuum suction port 122 is formed on the top of the cover by the top opening of the path 122a.

Next, the sampling method of the effusion fluid 131 with the use of the SEF sampling device 120 shown in FIG. 1 will be described.

First, an adhesive tape 132 is applied onto the annular area of the bottom of the base 121a around the sampling port 128.

Then, the surface of the adhesive tape 132 is applied to the skin surface 130 of an arm or other of a human body.

Thereafter, one (here, a left-hand side one) of the handles 143 is pushed along the skin surface 130 to slide the valve 124 until the corresponding handle 143 is contacted with the opposing area of the head 121b. At this point, the communication path 141 of the valve 124 is connected to the skin suction port 123 through the communication path 123a. At the same time, the communication path 141 is connected to the vacuum suction port 22 through the communication path 125a, the fluid reservoir 125, and the communication path 122a.

Further, the vacuum suction port 122 is connected to a vacuum pump (not shown) to thereby evacuate the inside of the cell 121, i.e., the reservoir 125 and the communication paths 123a, 141, 125a, and 122a. Thus, the effusion fluid 131 is sampled from or taken out of the skin surface 130. The fluid 131 is stored in the fluid reservoir 125 through the skin suction port 123 and the communication paths 123a, 141, and 125a.

Some other examples of the sampling device of this sort were disclosed in such the documents as the Japanese Non-Examined Utility Model Publication No. 2-1107 published in 1990, the Japanese Non-Examined Utility Model Publication No. 2-2648 published in 1990, the Japanese Non-Examined Utility Model Publication No. 2-20510 published in 1990, and the Japanese Non-Examined Patent Publication No. 4-253850 published in 1992. The conventional sampling devices disclosed in these documents are not provided with a slide valve, which is different from the present invention.

The above-described conventional SEF sampling device shown in FIG. 1 has some problems:

A first problem is that the operation efficiency in taking out the effusion fluid 131 stored in the fluid reservoir 125 is low. The reason is as follows.

To take out the effusion fluid 131 from the reservoir 125, it is required to close the slide valve 124 for releasing the vacuum in the reservoir 125 and then, to open the cover 142. Further, after taking out the fluid 131 from the reservoir 125, it is required for the next sampling process to close the cover 142 before evacuating the fluid reservoir 125, and to open the valve 124.

A second problem is that the effusion fluid 131 cannot be sampled from the skin surface 130 successively. This is because the vacuum must be released before taking out the effusion fluid 131 stored in the reservoir 125.

SUMMARY OF THE INVENTION

Accordingly, an object of the present invention is to provide a sampling device of the suction effusion fluid that is good in sampling operation efficiency.

Another object of the present invention is to provide a sampling device of the suction effusion fluid that is capable of successive sampling operation of the suction effusion fluid without releasing the vacuum of a vacuum suction port.

A sampling device of the suction effusion fluid according to the present invention includes a cell, a slide valve, and fluid reservoirs.

The cell has a vacuum suction port and a skin suction port. The vacuum suction port is designed to be connected to a vacuum source on operation. The skin suction port is designed to be opposite to a skin surface on operation.

The slide valve is formed in the cell to be movable in a plane approximately parallel to the skin surface. The slide valve is used for opening or closing a communication path communicating the skin suction port with the vacuum suction port.

The fluid reservoirs are formed in the slide valve. Each of the fluid reservoirs is alternately communicated with the skin suction port and the vacuum suction port through the communication path by sliding movement of the slide valve. Each of the fluid reservoirs is used for storing an effusion fluid acquired from the skin surface by vacuum suction through the skin suction port.

When the slide valve is located at a position where one of the fluid reservoirs is communicated with the skin suction port and the vacuum suction port, at least one of the remaining fluid reservoirs is exposed to the outside of the cell.

With the sampling device according to the present invention, the slide valve has the fluid reservoirs. Each of the fluid reservoirs is alternately communicated with the skin suction port and the vacuum suction port through the communication path by sliding movement of the slide valve. Also, when the slide valve is located at a position where one of the fluid reservoirs is communicated with the skin suction port and the vacuum suction port, at least one of the remaining fluid reservoirs is exposed to the outside of the cell.

Therefore, an operator or user of the device can readily access the effusion fluid stored in the at least one of the fluid reservoirs exposed to the outside of the cell with the use of a syringe or other, if only the slide valve is moved. This results in good operation efficiency of the sampling.

In addition, because each of the fluid reservoirs is alternately communicated with the skin suction port and the vacuum suction port by sliding movement of the slide valve, any one of the fluid reservoirs is able to be replaced with another while the airtight condition is maintained. Further, while the effusion fluid stored in the at least one of the fluid reservoirs exposed to the outside of the cell is taken out therefrom, the effusion fluid can be suction-sampled with the use of another one of said fluid reservoirs.

Thus, continuous or successive sampling of the effusion fluid can be performed without releasing the vacuum of the vacuum suction port.

Preferably, the slide valve is translatable along a straight line in the plane. In this case, it is preferred that the slide valve has a rod-like shape, and that the straight line is the longitudinal axis of the shape.

The slide valve is preferably turnable around an axis in the plane. In this case, it is preferred that the slide valve has a disk-like shape, and that the shaft is located at the center of the shape.

In a preferred embodiment according to the present invention, the slide valve has check valves for preventing the effusion fluid stored in the corresponding fluid reservoirs from back-flowing toward the skin suction port. The check valves are located at bottoms of the corresponding fluid reservoirs, respectively.

In another preferred embodiment according to the present invention, the slide valve has detachable cartridges. The fluid reservoirs are formed in the cartridges, respectively, so that the fluid reservoirs are detachable from the slide valve.

In still another preferred embodiment according to the present invention, the slide valve has the above-described detachable cartridges and the above-described check valves. The check valves are located at bottoms of the corresponding fluid reservoirs, and are detachable from the slide valve together with the corresponding cartridges, respectively.

In a further preferred embodiment according to the present invention, a valve for opening and closing the communication path communicating the skin suction port with the vacuum suction port is further provided. The valve is driven to be interlocked with sliding movement of the slide valve.

In this case, it is preferred that the valve opens the communication path when each of the fluid reservoirs is communicated with the skin suction port and the vacuum suction port, and the valve closes the communication path when none of the fluid reservoirs is communicated with the skin suction port and the vacuum suction port.

In a still further preferred embodiment according to the present invention, a first valve for opening and closing the skin suction port and a second valve for opening and closing the vacuum suction port are further provided. The first and second valves are driven to be interlocked with sliding movement of the slide valve.

In this case, it is preferred that the first and second valves open the communication path when each of the fluid reservoirs is communicated with the skin suction port and the vacuum suction port, and the first and second valves close the communication path when none of the fluid reservoirs is communicated with the skin suction port and the vacuum suction port.

BRIEF DESCRIPTION OF THE DRAWINGS

In order that the present invention maybe readily carried into effect, it will now be described with reference to the accompanying drawings.

DETAILED DESCRIPTION OF THE PREFERRED EMBODIMENTS

Figure 1:
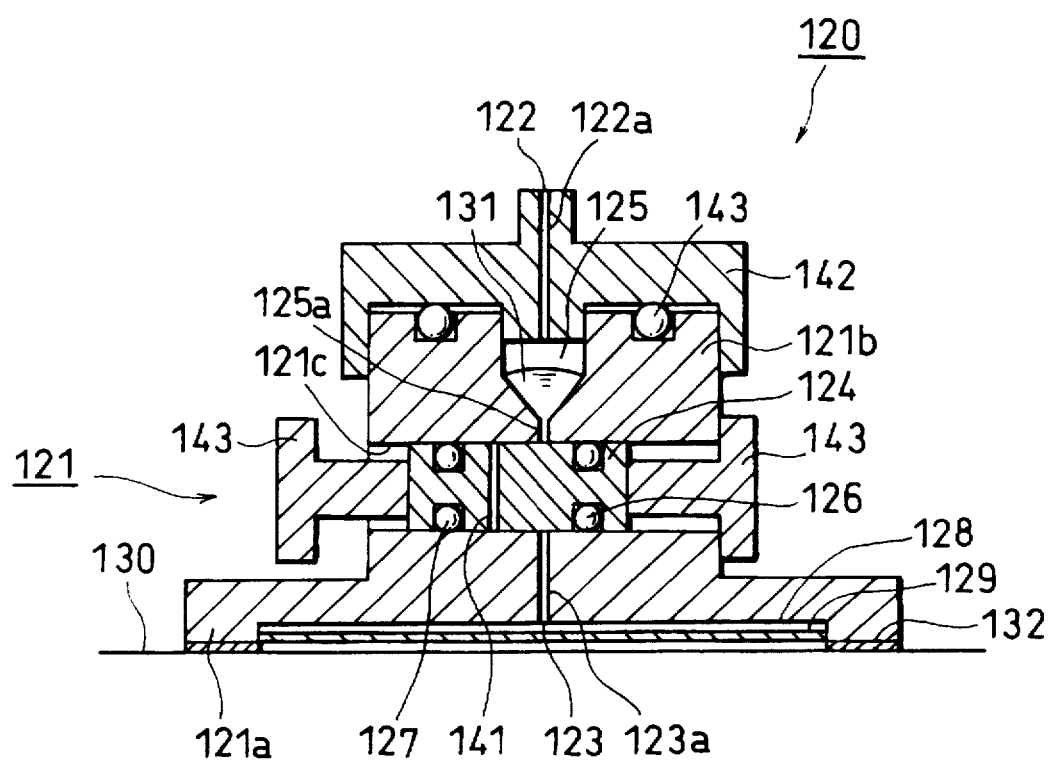
FIG. 1 is a cross-sectional view of a conventional sampling device of the suction effusion fluid.

Preferred embodiments of the present invention will be described below referring to the drawings attached.

FIRST EMBODIMENT

Figure 2:
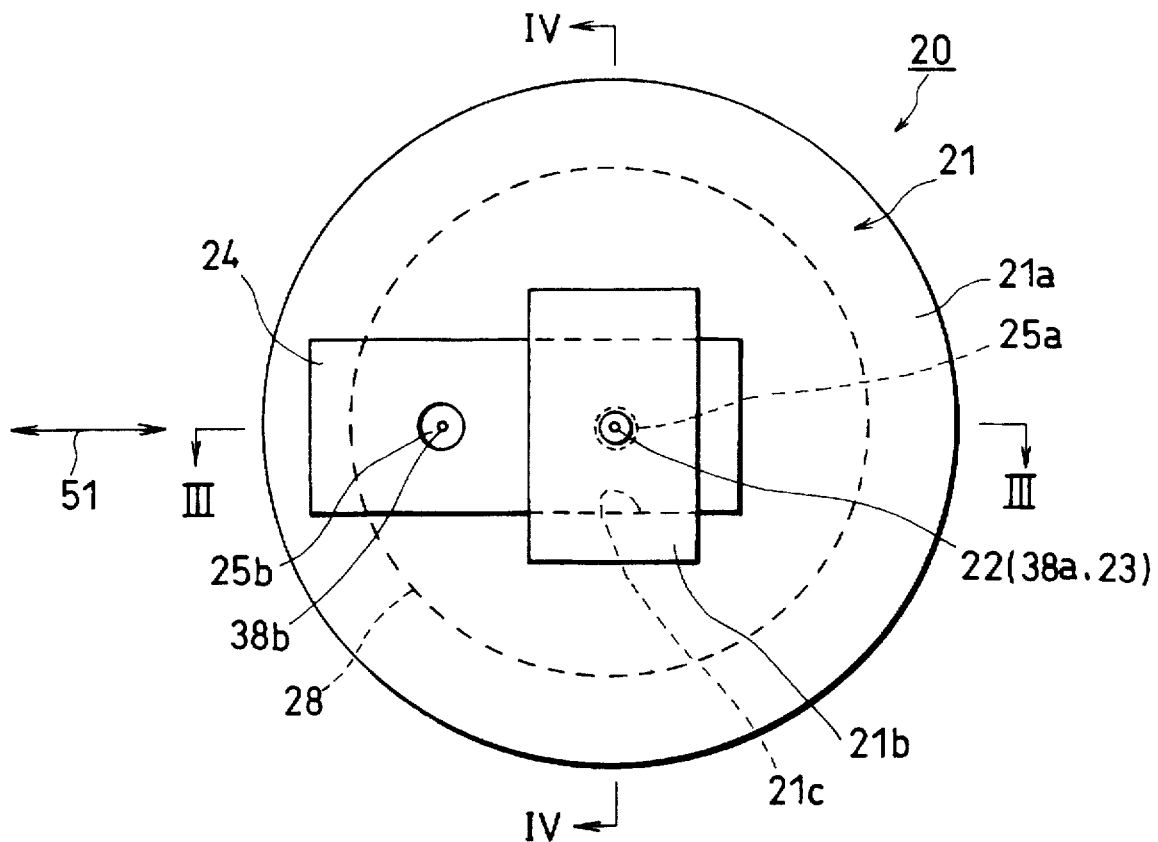
FIG. 2 is a plan view of a sampling device of the suction effusion fluid according to a first embodiment of the present invention.
Figure 3:
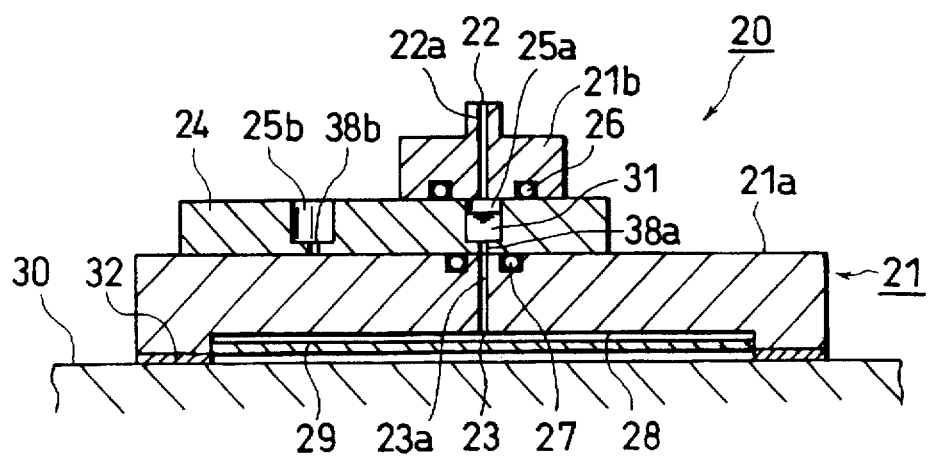
FIG. 3 is a cross-sectional view along the line III—III in FIG. 2.
Figure 4:
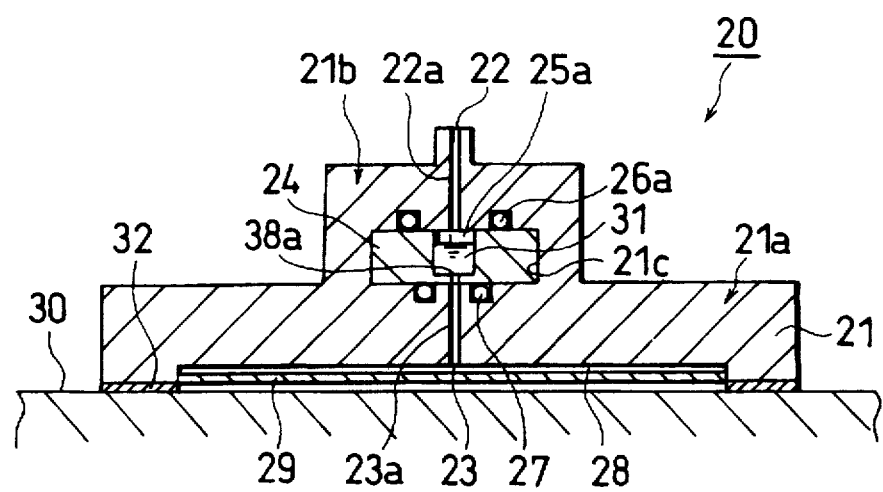
FIG. 4 is a cross-sectional view along the line IV—IV in FIG. 2.

A sampling device of the SEF according to a first embodiment is shown in FIGS. 2, 3, and 4.

The SEF sampling device 20 according to the first embodiment has a cell 21 made of a clear resin material. As the clear resin material, polyvinyl chloride, acrylic resin, or other is used.

The cell 21 is composed of a base 21a with a shape of a circular plate and a head 21b with a shape of a rectangular parallelepiped. The base 21a and the head 21b are formed to be integrated with each other. The size or dimension of the head 21b is far smaller than the diameter of the base 21a. The head 21b is concentric with the base 21a. In other words, the base 21a and the head 21b are concentric with the vertical, central common axis of the cell 21.

A circular recess 28 serving as a sampling port is formed on the bottom surface of the base 21a. A communication path 23a is formed in the base 21a to extend on the central axis of the cell 21. A skin suction port 23 is formed on the bottom surface of the base 21a in the sampling port 28. The port 23 is formed by the bottom opening of the communication path 23a.

A spacer 29 with fine meshes is attached to the base 21a in the recess or sampling port 28. The spacer 29 prevents the skin surface 30 from being tightly contacted with the skin suction port 23. The tight contact of the skin surface 30 makes it difficult to sample the effusion fluid 31 in vacuum suction.

The head 21b is provided with a rectangular hole 21c penetrating the head 21b in a direction perpendicular to the common central axis of the cell 21. A slide valve 24 with a rectangular cross-section (i.e., with a plate-like shape) is inserted and fitted into the hole 21c to linearly slide along the axis of the hole 21c.

The valve 24 has first and second cylindrical fluid reservoirs 25a and 25b for storing an effusion fluid 131. The two reservoirs 25a and 25b are laterally apart from each other in the valve 24. The tops of the reservoirs 25a and 25b are opened on the top end of the valve 24.

The valve 24 further has first and second communication paths 38a and 38b located beneath the first and second reservoirs 25a and 25b, respectively. The first path 38a is concentric with and communicated with the first reservoir 25a. The second path 38b is concentric with and communicated with the second reservoir 25b.

A communication path 22a is formed in the upper part of the head 21b to be concentric with the common central axis of the cell 21. The bottom end of the path 22a is communicated with the hole 21c. The top end of the path 22a is opened on the top surface of the head 21b, and forms a vacuum suction port 22. The communication path 22a and the vacuum suction port 22 are located right over the communication path 23a and the skin suction port 23. In other words, the paths 22a and 23a and the ports 22 and 23 are concentric with the central common axis of the cell 121.

A circular channel is formed in the lower, internal wall surface of the hole 21c for the valve 24. This channel is concentric with the communication path 23a. An O-ring 27 is fitted into the channel, and exposed to the hole 21c. The O-ring 27 has a function of sealing airtightly the gap between the slide 24 and the base 21a.

Another circular channel is formed in the upper, internal wall surface of the hole 21c This channel is also concentric with the communication path 23a. An O-ring 26 is fitted into the channel, and exposed to the hole 21c. The O-ring 26 has a function of sealing airtightly the gap between the slide 24 and the head 21b.

The first and second reservoirs 25a and 25b and the first and second communication paths 38a and 38b of the valve 24 are able to be alternately connected to or disconnected from the communication path 23a (i.e., the skin suction port 23) of the base 21a and the communication path 22a (i.e., the vacuum suction port 22) of the head 21b by linear sliding movement of the valve 24.

Specifically, when the valve 24 is located at a first position where the two paths 23a and 38a are overlapped with each other, as shown in FIG. 3, the first reservoir 25a and the first communication path 38a are connected to the communication paths 23a and 22a. When the valve 24 is located at a second position where the two paths 23a and 38b are overlapped with each other, the second reservoir 25b and the second communication path 38b are connected to the paths 23a and 22a. When the valve 24 is not located at the first and second points, both of the first and second reservoirs 25a and 25b are disconnected from the paths 23a and 22a.

As shown in FIGS. 2 and 3, when the slide valve 24 is located at the first point, the second fluid reservoir 25b is exposed to the outside of the cell 21. This position of the second reservoir 25b is a first position for sampling with a syringe or other.

On the other hand, when the slide valve 24 is located at the second point, the first fluid reservoir 25a is exposed to the outside of the cell 21. This position of the first reservoir 25a is a second position for sampling with a syringe or other.

Next, the sampling method of the effusion fluid 31 with the use of the SEF sampling device 20 according to the first embodiment of FIGS. 2, 3, and 4 will be described.

First, an adhesive tape 32 is applied onto the annular area of the bottom of the base 21a around the sampling port 28. Then, the surface of the adhesive tape 32 is applied to the skin surface 30 of an arm or other.

Thereafter, as shown in FIGS. 2 and 3, the slide valve 24 is linearly slid in a direction perpendicular to the central axis of the cell 21 to the first position where the first fluid reservoir 25a is communicated with the vacuum suction port 22 and the skin suction port 23. At this time, the second fluid reservoir 25b is exposed to the outside of the cell 21, being ready for sampling with a syringe or other.

Then, the vacuum suction port 22 is connected to a vacuum pump (not shown) to thereby evacuate the inside of the cell 21, i.e., the first reservoir 25a, the first communication path 38a, and the communication paths 23a and 25a. Thus, the effusion fluid 31 is sampled from or taken out of the skin surface 30. The fluid 31 is stored in the first fluid reservoir 25 through the skin suction port 23 and the communication paths 23a and 38a.

In this state, while the insides of the vacuum suction port 22 and the skin suction port 23 being kept airtight in the evacuated condition with the O-rings 26 and 27, the slide valve 24 is linearly slid in the direction perpendicular to the central axis of the cell 21 to the second position where the second fluid reservoir 25b is communicated with the vacuum suction port 22 and the skin suction port 23. At this time, the first fluid reservoir 25a is moved to the position where it is exposed to the outside of the cell 21, allowing the effusion fluid 31 stored in it to be sampled with a syringe or other.

At the same time, the second fluid reservoir 25b is immediately evacuated, and storing the effusion fluid 31 in the second fluid reservoir 25b is started.

By repeating this cycle of operation, the effusion fluid 31 can be successively sampled without releasing the vacuum.

With the SEF sampling device 20 according to the first embodiment, the slide valve 24 has the first and second fluid reservoirs 25a and 25b. Each of the fluid reservoirs 25a and 25b is alternately communicated with the skin suction port 23 and the vacuum suction port 22 through the communication paths 23a, 38a, 22a by linear sliding movement of the slide valve 24.

Also, when the slide valve 24 is located at the first position where the first reservoir 25a is communicated with the skin suction port 22 and the vacuum suction port 23, the second reservoir 25b is exposed to the outside of the cell 21.

Therefore, an operator or user of the device 20 can readily access the effusion fluid 31 stored in the first or second fluid reservoirs 25a or 25b exposed to the outside of the cell 21 With the use of a syringe or other, if only the slide valve 24 is moved. This results in good operation efficiency of the sampling.

In addition, because each of the first and second fluid reservoirs 25a and 25b is alternately communicated with the skin suction part 22 and the vacuum suction port 23 by sliding movement of the slide valve 24, any one of the fluid reservoirs 25a and 25b is able to be replaced w ith another while the airtight condition is maintained.

Further, while the effusion fluid 31 stored in the first or second fluid reservoir 25a and 25b exposed to the outside of the cell 21 is taken out therefrom, the effusion fluid 31 can he suction-sampled with the use of the second or first fluid reservoir 255b or 25a.

Thus, successive sampling of the effusion fluid 31 can be performed without releasing the vacuum of the vacuum suction port 22.

In the device 20 according to the first embodiment, the two fluid reservoirs 25a and 25b are internally provided in the slide valve 24. However, it is needless to say that the number of fluid reservoirs may be three or more.

It is sufficient that when the slide valve 24 is slid to the position where any one of fluid reservoirs is communicated with the vacuum suction port 22 and the skin suction port 23, at least one of the remaining fluid reservoirs is exposed to the outside of the cell 21.

SECOND EMBODIMENT

Figure 5:
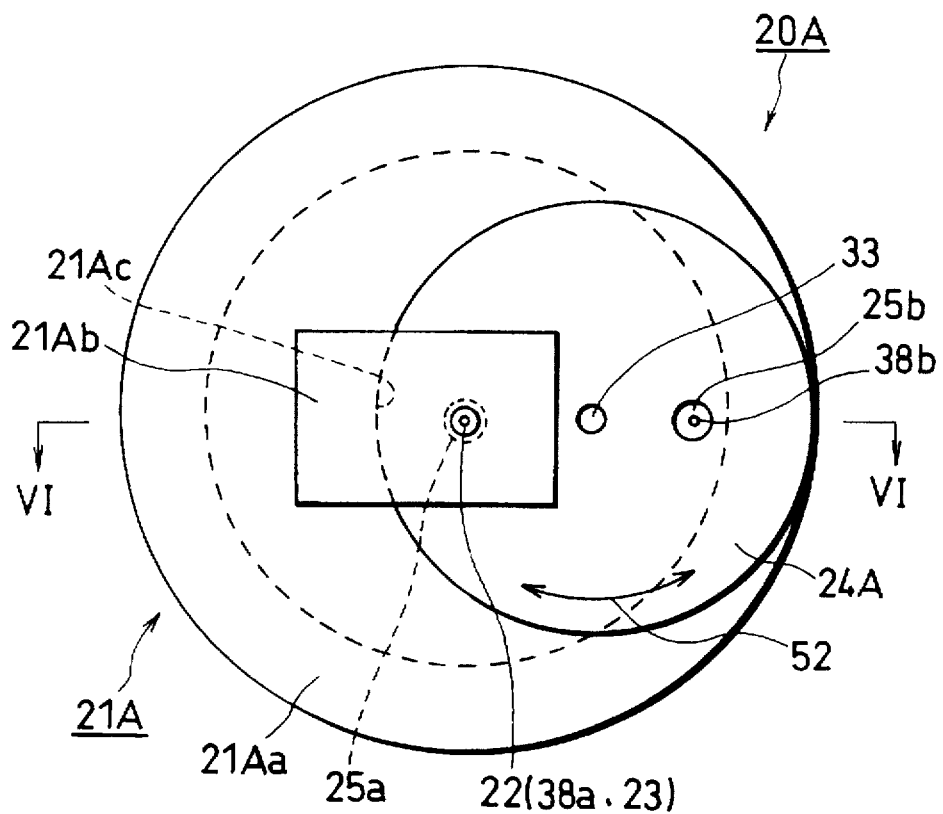
FIG. 5 is a plan view of a sampling device of the suction effusion fluid according to a second embodiment of the present invention.
Figure 6:
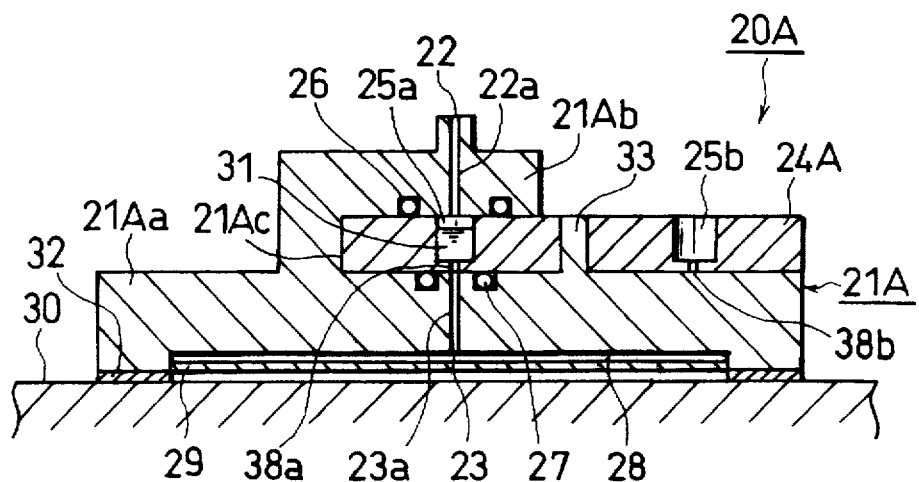
FIG. 6 is a cross-sectional view along the line VI—VI in FIG. 5.

A sampling device of the SEF according to a second embodiment is shown in FIGS. 5 and 6.

The SEF sampling device 20A according to the second embodiment has the same configuration as that according to the first embodiment of FIGS. 2, 3 and 4, except for the configurations of the cell and the slide valve. Therefore, for the sake of simplification of description, the explanation about the same configuration is omitted here by adding the same reference numerals to the corresponding elements or components having the same functions as those in the first embodiment.

In FIGS. 5 and 6, a slide valve 24A has a disk-like geometry, and is equipped with the first and second fluid reservoirs 25a and 25b therein. The reservoirs 25a and 25b are located at an equal distance or radius from the center of the valve 24A, and are in the opposite sides to the center thereof.

A cell 21A is integrally formed by a base 21Aa and a head 21Ab. The base 21Aa has a disc-like shape, which is the same as that of the first embodiment. However, unlike the first embodiment, the base 21Aa has a upward protruding shaft 33 for engaging the disk-shaped slide valve 24A and allowing the valve 24A to be turned around the shaft 33.

The head 21Ab has a shape of a rectangular parallelepiped which is similar to that of the first embodiment. However, the head 21Ab has a groove 21Ac into which the disk-shaped slide valve 24A is inserted. As shown in FIG. 5, the slide valve 24A is able to be slid and turned around the shaft 33 along an arrow 52.

The first and second reservoirs 25a and 25b and the first and second communication paths 38a and 38b of the valve 24A are able to be alternately connected to or disconnected from the skin suction port 23 of the base 21Aa and the vacuum suction port 22 of the head 21Ab by circular sliding movement of the valve 24A around the shaft 33.

Specifically, when the valve 24A is located at a first position where the two paths 23a and 38a are overlapped with each other, as shown in FIG. 6, the first reservoir 25a and the first communication path 38a are connected to the communication paths 23a and 22a. When the valve 24 is located at a second position where the two paths 23a and 38b are overlapped with each other, the second reservoir 25b and the second communication path 38b are connected to the paths 23a and 22a. When the valve 24A is not located at the first and second points, both of the first and second reservoirs 25a and 25b are disconnected from the paths 23a and 22a.

As shown in FIGS. 5 and 6, when the slide valve 24A is located at the first point, the second fluid reservoir 25b is exposed to the outside of the cell 21A. This position of the second reservoir 25b is a first position for sampling with a syringe or other.

On the other hand, when the slide valve 24A is located at the second point, the first fluid reservoir 25a is exposed to the outside of the cell 21. This position of the first reservoir 25a is a second position for sampling with a syringe or other.

Next, the sampling method of the effusion fluid 31 with the use of the SEF sampling device 20A according to the second embodiment of FIGS. 5 and 6 will be described below.

First, an adhesive tape 32 is applied onto the annular area of the bottom of the base 21Aa around the sampling port 28. Then, the surface of the adhesive tape 32 is applied to the skin surface 30 of an arm or other.

Thereafter, as shown in FIGS. 5 and 6, the slide valve 24A is circularly slid by 180° in a plane perpendicular to the central axis of the cell 21A to the first position where the first fluid reservoir 25a is communicated with the vacuum suction port 22 and the skin suction port 23. At this time, the second fluid reservoir 25b is exposed to the outside of the cell 21A, being ready for sampling with a syringe or other.

Then, the vacuum suction port 22 is connected to a vacuum pump (not shown) to thereby evacuate the inside of the cell 21A, i.e., the first reservoir 25a, the first communication path 38a, and the communication paths 23a and 25a. Thus, the effusion fluid 31 is sampled from or taken out of the skin surface 30. The fluid 31 is stored in the first fluid reservoir 25 through the skin suction port 23 and the communication paths 23a and 38a.

In this state, while the insides of the vacuum suction port 22 and the skin suction port 23 being kept airtight in the evacuated condition with the O-rings 26 and 27, the slide valve 24A is circularly slid in the plane perpendicular to the central axis of the cell 21A to the second position where the second fluid reservoir 25b is communicated with the vacuum suction port 22 and the skin suction port 23. At this time, the first fluid reservoir 25a is moved to the position where it is exposed to the outside of the cell 21A, allowing the effusion fluid 31 stored in it to be sampled with a syringe or other.

At the same time, the second fluid reservoir 25b is immediately evacuated, and storing the effusion fluid 31 in the second fluid reservoir 25b is started.

By repeating this cycle of operation, the effusion fluid 31 can be successively sampled without releasing the vacuum.

With the SEF sampling device 20A according to the second embodiment, each of the first and second fluid reservoirs 25a and 25b is alternately communicated with the skin suction port 23 and the vacuum suction port 22 through the communication paths 23a, 38a, 22a by circular sliding movement of the disc-shaped slide valve 24A.

Also, when the slide valve 24A is located at the first position where the first reservoir 25a is communicated with the skin suction port 22 and the vacuum suction port 23, the second reservoir 25b is exposed to the outside of the cell 21A.

Therefore, an operator or user of the device 20 can readily access the effusion fluid 31 stored in the first or second fluid reservoirs 25a or 25b exposed to the outside of the cell 21A with the use of a syringe or other, if only the slide valve 24A is moved. This results in good operation efficiency of the sampling.

In addition, because each of the first and second fluid reservoirs 25a and 25b is alternately communicated with the skin suction port 22 and the vacuum suction port 23 by sliding movement of the slide valve 24A, any one of the fluid reservoirs 25a and 25b is able to be replaced with another while the airtight condition is maintained.

Further, while the effusion fluid 31 stored in the first or second fluid reservoir 25a and 25b exposed to the outside of the cell 21A is taken out therefrom, the effusion fluid 31 can be suction-sampled with the use of the second or first fluid reservoir 25b or 25a.

Thus, successive or continuous sampling of the effusion fluid 31 can be performed without releasing the vacuum of the vacuum suction port 22.

In the second embodiment also, it is needless to say that the number of fluid reservoirs may be three or more.

THIRD EMBODIMENT

Figure 7:
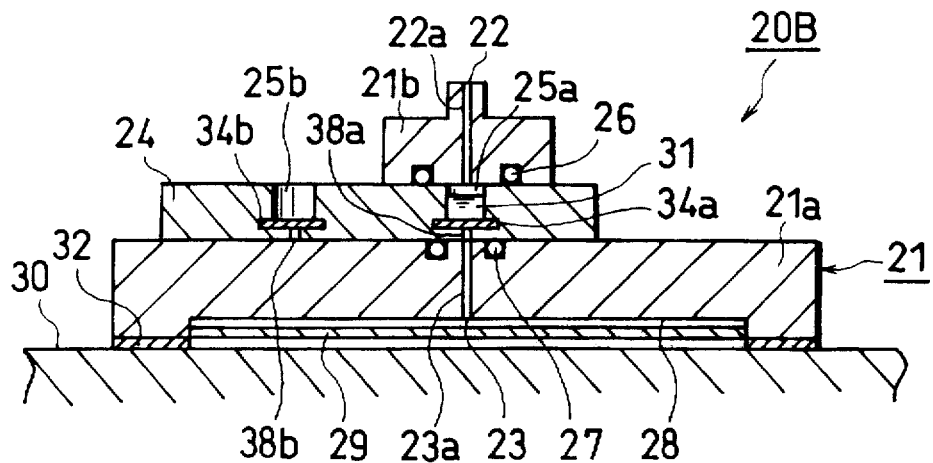
FIG. 7 is a cross-sectional view of a sampling device of the suction effusion fluid according to a third embodiment of the present invention, which shows the same cross section as that of FIG. 3.

A sampling device of the SEF according to a third embodiment is shown in FIG. 7.

The SEF sampling device 20B according to the third embodiment has the same configuration as that according to the first embodiment of FIGS. 2, 3 and 4, except that first and second check valves 34a and 34b are additionally provided in the valve 24. Therefore, for the sake of simplification of description, the explanation about the same configuration is omitted here by adding the same reference numerals to the corresponding elements or components having the same functions as those in the first embodiment.

As shown in FIG. 7, the first and second check valves 34a and 34b are located at the bottoms of the first and second fluid reservoirs 25a and 25b, respectively. The valves 34a and 34b are opened when the insides of the first and second fluid reservoirs 25a and 25b are evacuated, and closed when the vacuum is released, respectively. The first and second check valves 34a and 34b have a function of positively preventing the effusion fluid 31 from back-flowing when the effusion fluid 31 stored in the first and second fluid reservoirs 25a and 25b is moved to the positions for sampling with a syringe or other, respectively.

Therefore, in addition to the advantages in the first embodiment, the sampling device 20B has an additional advantage that the effusion fluid 31 stored in the first and second fluid reservoirs 25a and 25b is prevented from back-flowing at the first and second sampling positions.

FOURTH EMBODIMENT

Figure 8:
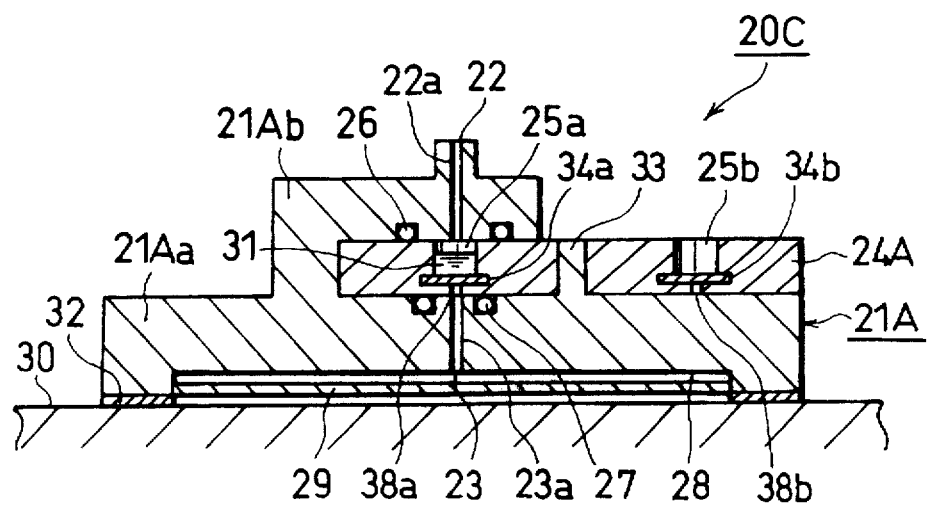
FIG. 8 is a cross-sectional view of a sampling device of the suction effusion fluid according to a fourth embodiment of the present invention, which shows the same cross section as that of FIG. 6.

A sampling device of the SEF according to a fourth embodiment is shown in FIG. 8.

The SEF sampling device 20C according to the fourth embodiment has the same configuration as that according to the second embodiment of FIGS. 5 and 6, except that first and second check valve 34a and 34b are additionally provided in the turnable, circular valve 24A Therefore, for the sake of simplification of description, the explanation about the same configuration is omitted here by adding the same reference numerals to the corresponding elements or components having the same functions as those in the second embodiment.

As shown in FIG. 8, the first and second check valves 34a and 34b are located at the bottoms of the first and second fluid reservoirs 25a and 25b, respectively.

The function and advantage of the valves 34a and 34b are the same as those of the third embodiment of FIG. 7, respectively, and therefore, the explanation about the check valves 34a and 34b is omitted here.

FIFTH EMBODIMENT

Figure 9:
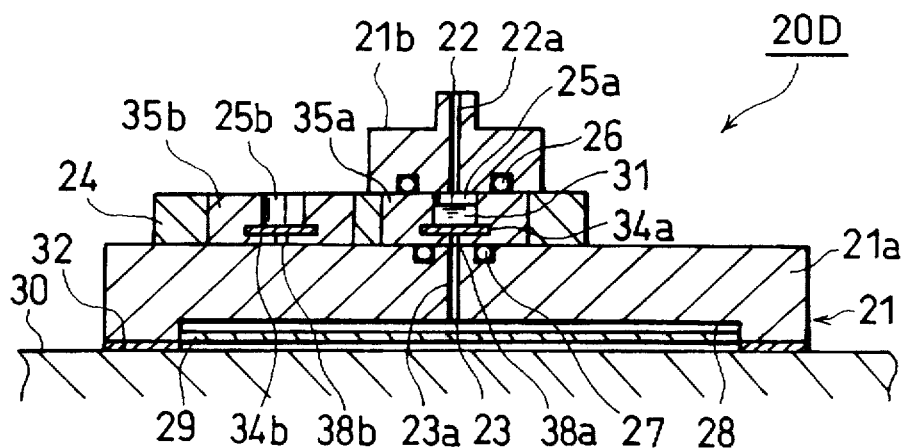
FIG. 9 is a cross-sectional view of a sampling device of the suction effusion fluid according to a fifth embodiment of the present invention, which shows the same cross section as that of FIG. 3.

A sampling device of the SEF according to a fifth embodiment is shown in FIG. 9.

The SEF sampling device 20D according to the fifth embodiment has the same configuration as that according to the first embodiment of FIGS. 2, 3 and 4, except that first and second detachable cartridges 35a and 35b are additionally provided in two holes of the valve 24, and that the first and second cartridges 35a and 35b have the first and second reservoirs 25a and 25b and first and second check valves 34a and 34b, respectively. The check valves 34a and 34b are located at the bottoms of the reservoirs 25a and 25b in the cartridges 35a and 35b, respectively.

Therefore, the explanation about the same configuration is omitted here by adding the same reference numerals to the corresponding elements or components having the same functions as those in the first embodiment.

In the sampling device according to the fifth embodiment, there arises an additional advantage that the need for use of a syringe or other is eliminated by detaching and replacing the cartridge 35a or 35b storing the effusion fluid 31 with a new one when it is moved to the first or second sampling positions.

Further, there arises another additional advantage that the constituents of the sampled effusion fluid 31 are able to be determined by loading the cartridge 35a or 35b including the effusion fluid 31 in a measuring system (not shown).

SIXTH EMBODIMENT

Figure 10:
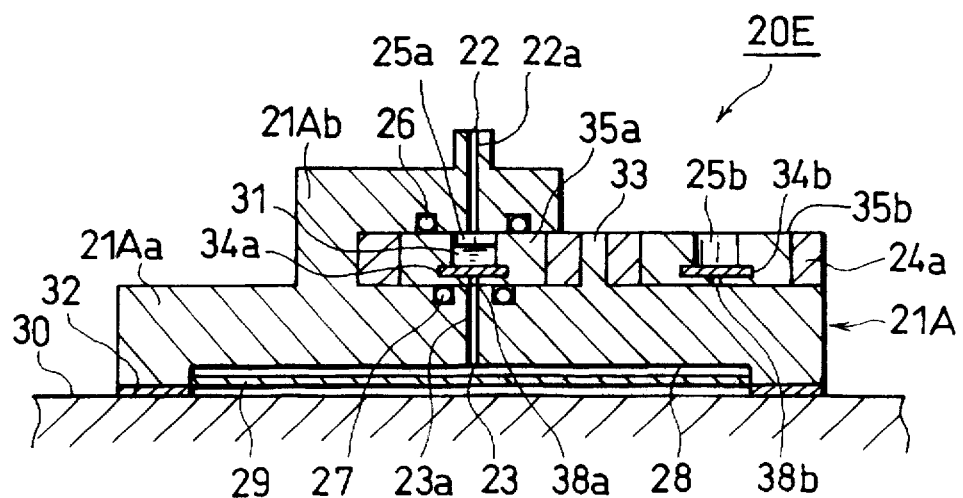
FIG. 10 is a cross-sectional view of a sampling device of the suction effusion fluid according to a sixth embodiment of the present invention, which shows the same cross section as that of FIG. 6.

A sampling device of the SEF according to a sixth embodiment is shown in FIG. 10.

The SEF sampling device 20E according to the sixth embodiment has the same configuration as that according to the second embodiment of FIGS. 5 and 6, except that first and second detachable cartridges 35a and 35b are additionally provided in the disc-shaped valve 24A. and that the first and second cartridges 35a and 35b have the first and second reservoirs 25a and 25b and first and second check valves 34a and 34b, respectively. The check valves 34a and 34b are located at the bottoms of the reservoirs 25a and 25b in the cartridges 35a and 35b, respectively.

Therefore, the explanation about the same configuration is omitted here by adding the same reference numerals to the corresponding elements or components having the same functions as those in the second embodiment.

In the sampling device according to the sixth embodiment, there arises the same additional advantages as those in the fifth embodiment.

SEVENTH EMBODIMENT

Figure 11:
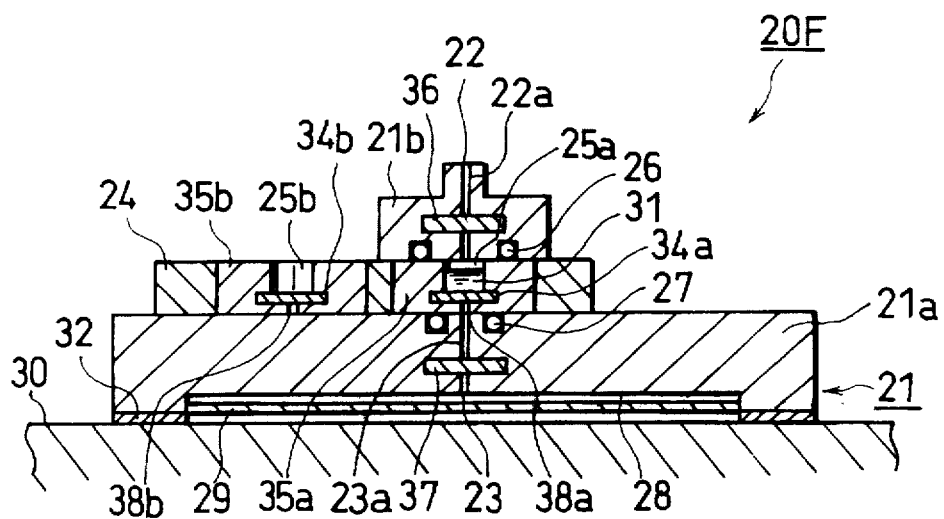
FIG. 11 is a cross-sectional view of a sampling device of the suction effusion fluid according to a seventh embodiment of the present invention, which shows the same cross section as that of FIG. 3.

A sampling device of the SEF according to a seventh embodiment is shown in FIG. 11.

The SEF sampling device 20F according to the seventh embodiment has the same configuration as that according to the fifth embodiment of FIG. 9, except that first and second on-off valves 36 and 37 that open and close the vacuum suction port 22 and the skin suction port 23, respectively. The valves 36 and 37 are operated to be interlocked with the linear sliding movement of the rod-shaped slide valve 24. This interlock may be realized by a known mechanical or electrical linkage mechanism (not shown).

Therefore, the explanation about the same configuration is omitted here by adding the same reference numerals to the corresponding elements or components having the same functions as those in the fifth embodiment.

The first on-off valve 36 is fixed in the communication path 23a of the base 21a to open and close the path 23a communicated with the skin suction port 23. The second on-off valve 37 is fixed in the communication path 22a of the head 21b to open and close the path 22a communicated with the vacuum suction port 22.

When the first or second fluid reservoir 25a or 25b is moved to the first or second position where it can be communicated with the vacuum suction port 22 and the skin suction port 23, the first and second on-off valves 36 and 37 are opened. As a result, the fluid reservoir 25a or 25b is communicated with the vacuum suction port 22 and the skin suction port 23.

When the slide valve 24 is linearly moved to any position other than the first and second positions, the first and second on-off valves 36 and 37 are closed.

Thus, there arises an additional advantage that the airtight condition during switching over from the cartridge 35a to 35b or vice versa can be positively maintained in the seventh embodiment.

EIGHTH EMBODIMENT

Figure 12:
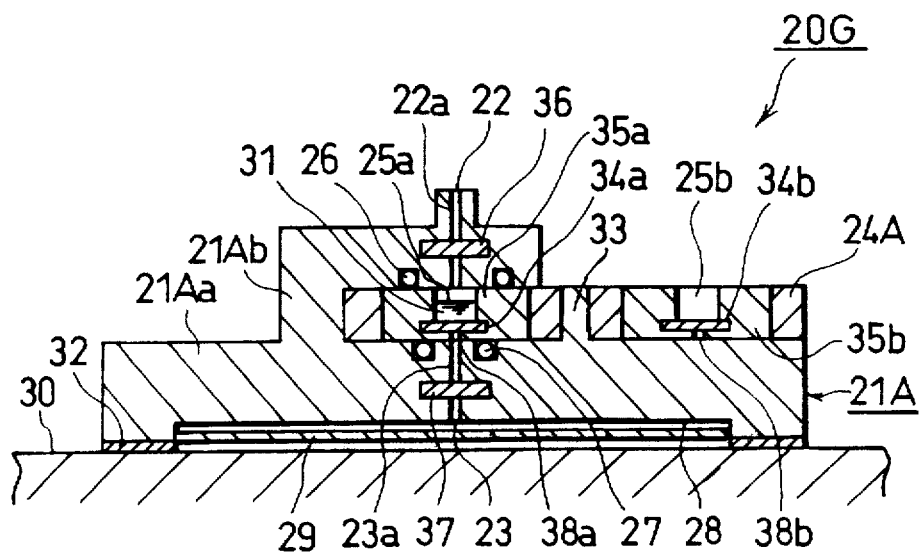
FIG. 12 is a cross-sectional view of a sampling device of the suction effusion fluid according to an eighth embodiment of the present invention, which shows the same cross section as that of FIG. 6.

A sampling device of the SEF according to an eighth embodiment is shown in FIG. 12.

The SEF sampling device 20G according to the eighth embodiment has the same configuration as that according to the sixth embodiment of FIG. 10, except that first and second on-off valves 36 and 37 that open and close the vacuum suction port 22 and the skin suction port 23, respectively. The valves 36 and 37 are operated to be interlocked with the linear sliding movement of the disk-shaped slide valve 24A.

This interlock may be realized by a known mechanical or electrical linkage mechanism (not shown).

Therefore, the explanation about the same configuration is omitted here by adding the same reference numerals to the corresponding elements or components having the same functions as those in the sixth embodiment.

Since the function of the first and second on-off valves 36 and 37 are the same as that of the seventh embodiment, no explanation is stated here again.

An additional advantage obtained in the eighth embodiment is the same as that of the seventh embodiment and therefore, the description is omitted.

The present invention is not limited to the abovedescribed embodiments. For example, the geometry of the slide valve is not limited to the rod- and disk-shaped ones. Any other geometry may be adopted, if wore than one fluid reservoir is provided in the slide valve.

While the preferred forms of the present invention have been described, it is to be understood that modifications will be apparent to those skilled in the art without departing from the spirit of the invention. The scope of the invention, therefore, is to be determined solely by the following claims.

What is claimed is:

1. A sampling device of a suction effusion fluid including:
   (a) a cell having a vacuum suction port and a skin suction port;
      said vacuum suction port being designed to be connected to a vacuum source on operation;
      said skin suction port being designed to be opposite to a skin surface on operation;
   (b) a slide valve formed in said cell to be movable in a plane approximately parallel to said skin surface;
      said slide valve being used for opening or closing a communication path communicating said skin suction port with said vacuum suction port without releasing the vacuum source of said vacuum suction port to maintain an airtight condition; and
   (c) a plurality of fluid reservoirs formed in said slide valve;
      each of said fluid reservoirs being alternately communicated with said skin suction port and said vacuum suction port through said communication path by sliding movement of said slide valve;
      each of said fluid reservoirs being used for storing an effusion fluid acquired from said skin surface by vacuum suction through said skin suction port;
      wherein said fluid reservoirs are formed in said slide valve; and
      wherein when said slide valve is located at a position where one of said fluid reservoirs is communicated with said skin suction port and said vacuum suction port, at least one of said remaining fluid reservoirs is exposed to the outside of the cell.

2. A device as claimed in claim 1, wherein said slide valve is translatable along a straight line in said plane.

3. A device as claimed in claim 2, wherein said slide valve has a rod-like shape;
   and wherein said straight line is a longitudinal axis of said shape.

4. A device as claimed in claim 1, wherein said slide valve is turnable around an axis in said plane.

5. A device as claimed in claim 4, wherein said slide valve has a disk-like shape;
   and wherein said shaft is located at the center of said shape.

6. A device as claimed in claim 1, wherein said slide valve has check valves for preventing said effusion fluid stored in said corresponding fluid reservoirs from back-flowing toward said skin suction port;
   and wherein said check valves are located at bottoms of said corresponding fluid reservoirs, respectively.

7. A device as claimed in claim 1, wherein said slide valve has detachable cartridges;
   and wherein said fluid reservoirs are formed in said cartridges, respectively, so that said fluid reservoirs are detachable from said slide valve.

8. A device as claimed in claim 1, wherein said slide valve has detachable cartridges;
   and wherein said fluid reservoirs are formed in said corresponding cartridges, respectively, so that said fluid reservoirs are detachable from said slide valve;
   and wherein each of said cartridges has a check valve for preventing said effusion fluid stored in a corresponding one of said fluid reservoirs from flowing toward said skin suction port;
   and wherein said check valves are located at bottoms of said corresponding fluid reservoirs, respectively;
   and wherein said check valves are detachable from said slide valve together with said corresponding cartridges, respectively.

9. A device as claimed in claim 1, further comprising a valve for opening and closing said communication path communicating said skin suction port with said vacuum suction port;
   said valve is driven to be interlocked with sliding movement of said slide valve.

10. A device as claimed in claim 9, wherein said valve opens said communication path when each of said fluid reservoirs is communicated with said skin suction port and said vacuum suction port;
   and wherein said valve closes said communication path when none of said fluid reservoirs is communicated with said skin suction port and said vacuum suction port.

11. A device as claimed in claim 1, further comprising:
   a first valve for opening and closing said skin suction port; and
   a second valve for opening and closing said vacuum suction port;
   wherein said first and second valves are driven to be interlocked with sliding movement of said slide valve.

12. A device as claimed in claim 11, wherein said first and second valves open said communication path when each of said fluid reservoirs is communicated with said skin suction port and said vacuum suction port;
   and wherein said first and second valves close said communication path when none of said fluid reservoirs is communicated with said skin suction port and said vacuum suction port.

13. A sampling device of a suction effusion fluid including:
   (a) a cell having a vacuum suction port and a skin suction port;
      said vacuum suction port being designed to be connected to a vacuum source on operation;
      said skin suction port being designed to be opposite to a skin surface on operation;
   (b) a plurality fluid reservoir formed in said cell to be communicated with said skin suction port and said vacuum suction port;

said fluid reservoir being used for storing an effusion fluid acquired from said skin surface by vacuum suction through said skin suction port; and (c) a slide valve formed in said cell to be movable in a plane approximately parallel to said skin surface;
   said slide valve being used for opening or closing a path communicating said skin suction port with said vacuum, suction port;
   characterizing in that
   said slide valve has fluid reservoirs;

each of said fluid reservoirs is alternately communicated with said skin suction port and said vacuum suction port through said path; and when said slide valve is located at a position where any one of said fluid reservoirs is communicated to said skin suction port and said vacuum suction port, at least one of said remaining fluid reservoirs is exposed to the outside of said cell.

* * * * *